United States Patent [19]
Siegrist et al.

[11] Patent Number: 5,883,253
[45] Date of Patent: Mar. 16, 1999

[54] PROCESS FOR THE PREPARATION OF AROMATIC O-SULFOCARBOXYLIC ACIDS AND SULFONYLUREAS

[75] Inventors: Urs Siegrist, Eiken; Manfred Müller, Dagmersellen; Jean Brünisholz, Antagnes/Ollon, all of Switzerland

[73] Assignee: Novartis AG, Basel, Switzerland

[21] Appl. No.: 860,149

[22] PCT Filed: Dec. 11, 1995

[86] PCT No.: PCT/EP95/04865

§ 371 Date: Jun. 19, 1997

§ 102(e) Date: Jun. 19, 1997

[87] PCT Pub. No.: WO96/19443

PCT Pub. Date: Jun. 27, 1996

[30] Foreign Application Priority Data

Dec. 22, 1994 [CH] Switzerland ............... 3896/94

[51] Int. Cl.$^6$ ............................. C07D 251/02
[52] U.S. Cl. ............... 544/211; 544/317; 544/327; 548/262.6
[58] Field of Search ............ 558/353; 544/211, 544/317, 327; 548/262.6

[56] References Cited

U.S. PATENT DOCUMENTS

| | | | |
|---|---|---|---|
| 4,454,355 | 6/1984 | Schubert et al. | 568/584 |
| 4,954,657 | 9/1990 | Heise et al. | 568/584 |
| 5,047,538 | 9/1991 | Domagala et al. | 546/156 |
| 5,550,237 | 8/1996 | Vermehren . | |

FOREIGN PATENT DOCUMENTS

| | | |
|---|---|---|
| 0584043 | 2/1994 | European Pat. Off. . |
| 2634419 | 2/1977 | Germany . |
| 3120912 | 12/1982 | Germany . |
| 3737919 | 5/1989 | Germany . |
| 4411682 | 10/1995 | Germany . |
| 1539183 | 6/1976 | United Kingdom . |

OTHER PUBLICATIONS

Journal of Organic Chemistry, vol. 45, No. 12, 1980 pp. 2365–2368.

Beyer–Walter, *Lehrbuch d. org. Chemie 21:* pp. 551, 553 & 559 (1988).

*Drugs of the Future* 18 (8): pp. 717–720 (1993).

Barry, J., et al, "Solid–Liquid Phase–Transfer Catalysis without Added Solvent, A Simple, Efficient, and Inexpensive . . . " Synthesis, Jan.: pp. 40–45 (1985).

*Primary Examiner*—Samuel Barts
*Attorney, Agent, or Firm*—Joseph Borovian; William A. Teoli, Jr.

[57] ABSTRACT

The invention relates to a process for the prepn of ortho-sulfocarboxylic acids, which comprises: a) in a first reaction step, diazotizing an aromatic o-aminosulfonic acid in the presence of an acid and nitrite in water, in an organic solvent or in a mixture thereof, to an o-diazonium sulfonate, and, b) in a second reaction step, reacting the o-diazonium sulfonate in the presence of a palladium catalyst in water, in an organic solvent or in a mixture thereof, with carbon monoxide, under overpressure, to an aromatic o-sulfocarboxylic acid. The invention also relates to a process for the preparation of sulfonylureas using o-sulfocarboxylic acids as intermediates. Thus, 4-methoxyaniline-2-sulfonic acid was diazotized and treated with CO to give 97% 4-methoxybenzoic acid 2-sulfonic acid.

21 Claims, No Drawings

PROCESS FOR THE PREPARATION OF AROMATIC O-SULFOCARBOXYLIC ACIDS AND SULFONYLUREAS

This is a 371 application of PCT/EP95/04865 filed Dec. 11, 1995.

The invention relates to a process for the preparation of aromatic ortho-sulfocarboxylic acids by diazotisation and subsequent palladium-catalysed carbonylation of aromatic aminosulfonic acids. The process is particularly suitable for the preparation of ortho-sulfobenzoic acids. The invention also relates to a process for the preparation of sulfonylureas using the ortho-sulfocarboxylic acids as intermediates.

Ortho-sulfobenzoic acids are important intermediates for the preparation of saccharin derivatives which can be used as pharmaceutical products. WO 90/13549 proposes, for example, the use of substituted saccharin derivatives as enzyme inhibitors for the treatment of degenerative diseases.

Saccharin has also long been used as sweetener, and its preparation and properties are described, inter alia, in Ullmanns Enzyklopädie der technischen Chemie, Vol. 22, 353–357, 1982.

Ortho-sulfobenzoic acids are also valuable intermediates for the preparation of acid dyes for textiles, in particular of wool and polyamide dyes.

Another important field in which ortho-sulfobenzoic acids find utility as intermediates is that of the agrochemicals, in particular herbicides of the sulfonylurea type disclosed, inter alia, in EP-A-0496 701.

Ortho-sulfobenzoic acids at the present time are prepared mainly by oxidation of the corresponding toluenesulfonic acids, using bichromate in concentrated sulfuric acid or potassium permanganate for the oxidation. This is described, inter alia, in Ullmanns Enzyklopädie der technischen Chemie, Vol. 22, 356,1982. Beilstein Vol. 11, 414 (1928), for example, specifically describes the oxidation of 4-methoxy-1-methylbenzene-2-sulfonic acid with $KMnO_4$.

The reaction conditions are drastic and have serious drawbacks with respect to ecology and industrial hygiene, such as heavy metal pollutants which have to be disposed of, as well as the use of concentrated acids, so that special protective measures and methods of disposal are required.

In particular, these processes are unsuitable for the economic preparation of substituted ortho-sulfocarboxylic acids, since a great number of by-products are formed under such reaction conditions, so that the reaction mixture is often obtained in the form of a dark oil or even in the form of tar. Furthermore, the processing of manganese- or chromium-containing waste acid poses another problem which can only be solved using elaborate technology, e.g. electrolysis for the recovery of chromium oxide.

A further process for the preparation of ortho-sulfobenzoic acids, the so-called Maumee process, is described, inter alia, in WO 90/13549. In this process, the sulfite is first prepared from diazotised anthranilic acid in a Sandmeier reaction with $SO_2$ and then oxidised with $Cl_2$. This, too, is a multistep reaction with educts which are difficult to handle and yields which are too low.

In J. Org. Chem., 45, 2365 (1980) and 46, 4413 (1981), Matsuda et al. describe the palladium-catalysed carbonylation of diazonium salts. The reaction is carried out in the presence of a palladium acetate catalyst in an aprotic solvent, e.g. acetonitrile, resulting in the case of the 4-methoxy diazonium salt, used in the form of its tetrafluoroborate, in a 58% yield of 4-methoxy benzoic acid. If protic solvents, e.g. alcohols, are used, a substantial loss in selectivity is observed and, inter alia, ester and free acid are obtained. The reaction is carried out in the presence of acetate, giving first a mixed anhydride which is then hydrolysed to the free acid. At higher reaction temperatures formation of tar is often observed, which renders the catalyst ineffective and results in a considerably reduced yield.

The carbonylation of aromatic ortho-sulfobenzodiazonium salts to the corresponding aromatic ortho-sulfocarboxylic acids is so far not known.

Surprisingly, it has now been found that the internal salt which forms during the diazotisation of aromatic o-aminosulfonic acids is very stable so that no additional anion, e.g. tetrafluoroborate, needs to be used for the stabilisation. For this reason, ortho-sulfobenzoic acids can be obtained in high yield and purity by subsequent palladium-catalysed carbonylation.

As no additional stabilising anion needs to be used, the amount of the by-products and waste products to be disposed of is also reduced, thereby constituting an important advantage of the process.

Diazonium salts are usually not very heat-stable and are therefore risky to use in large-scale industrial processes. In this respect the ortho-sulfobenzodiazonium salts constitute a considerably lower risk.

The cited advantages of high yield and purity are only achieved if ortho-diazonium sulfonates are used for the carbonylation.

The reaction proceeds with high selectivity also in protic solvents. No formation of tar, which could deactivate the catalyst, is observed. The process is therefore admirably suited for the large-scale industrial production of e.g. herbicides, dyes or saccharins, as the yield and purity of the intermediates are in these cases of decisive importance for the efficiency of the process.

Another advantage is that in many cases these diazonium salts can be further processed direct without isolation. This one-pot process permits particularly efficient processing.

However, it is also possible to isolate the diazonium salts and then to carry out the carbonylation. This feature also illustrates to advantage the special property of ortho-diazobenzenesulfonic acids to form stable internal salts, so that no additional anions have to be introduced into the process.

By virtue of the inherent stability of the diazonium compounds, the carbonylation can even be carried out at elevated temperature, for example at 60° C., and in the presence of protic solvents such as water. Surprisingly, $PdCl_2$ can also be used as catalyst, whereas in the process described by Matsuda in J. Org. Chem., 45, 2365 (1980) and 46, 4413 (1981) the costly Pd acetate must always be used as Pd precursor.

In one of its aspects the invention relates to a process for the preparation of ortho-sulfocarboxylic acids, which comprises a) in a first reaction step, diazotising an aromatic ortho-aminosulfonic acid in the presence of an acid and nitrite in water, in an organic solvent or in a mixture thereof, to an ortho-diazonium sulfonate, and, b) in a second reaction step, reacting the ortho-diazonium sulfonate in the presence of a palladium catalyst in water, in an organic solvent or in a mixture thereof, with carbon monoxide, under overpressure, to an aromatic ortho-sulfocarboxylic acid.

The aromatic aminosulfonic acids can be substituted by any groups which are inert during the reaction.

The sulfocarboxylic acids preferably contain one or two substituents $R_1$ and $R_2$ attached at the aromatic ring, and $R_1$ and $R_2$ are each independently of the other —Y, —COOH, —COOY, —CONH$_2$, —CONHY, —CONY$_2$, —C(O)Y, —CN, —NO$_2$, halogen, —OY, —SY, —SOY, —SO$_2$Y, SO$_3$Y, —NHCOY, —NR$_3$R$_4$, —C≡—C—R$_5$, —O—CHR$_6$—C≡—C—R$_5$, —CSY, —CSOY;

Y is hydrogen, phenyl, or linear or branched C$_1$–C$_6$alkyl which is unsubstituted or substituted by 1–4 halogen atoms, C$_1$–C$_3$alkoxy or C$_1$–C$_3$alkylthio; C$_2$–C$_6$alkenyl which is unsubstituted or substituted by 1–4 halogen atoms, and R$_3$ is hydrogen, CH$_3$O—, CH$_3$CH$_2$O— or C$_1$–C$_3$alkyl;

R$_4$ is hydrogen or C$_1$–C$_3$alkyl;

R$_5$ is hydrogen, methyl or ethyl;

R$_6$ is hydrogen or methyl.

Within the scope of this invention, the terms aromatic aminosulfonic acids and aromatic sulfocarboxylic acids will be understood to mean those aromatic hydrocarbons which obey the Hückel 4n+2 electron rule, typically benzenes, biphenyls and polycyclic hydrocarbons, e.g. tetralin, naphthalene, anthracene, indene.

Nitrite can be used in the form of its inorganic salts, typically the Li, Na or Ka salts, or in the form of an organic nitrite. Suitable organic nitrites are aliphatic nitrites, preferably C$_1$–C$_{12}$alkylnitrites.

A preferred process is that which comprises a) in a first reaction step, diazotising an aromatic ortho-aminosulfonic acid of formula I

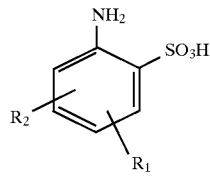

(I)

in the presence of an acid and nitrite in water, in an organic solvent or in a mixture thereof, to an ortho-diazonium sulfonate of formula II

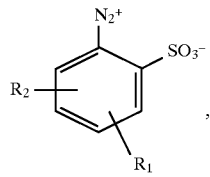

(II)

and, b) in a second reaction step, reacting the ortho-diazonium sulfonate of formula II in the presence of a palladium catalyst in water, in an organic solvent or in a mixture thereof, with carbon monoxide, under overpressure, to an ortho-sulfobenzoic acid of formula III

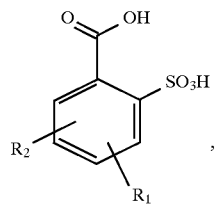

(III)

wherein

R$_1$ and R$_2$ are each independently of the other —Y, —COOH, COOY, —CONH$_2$, —CONHY, —CONY$_2$, —C(O)Y, —CN, —NO$_2$, halogen, —OY, —SY, —SOY, —SO$_2$Y, SO$_3$Y, —NHCOY, —NR$_3$R$_4$, —C≡C—R$_5$, —O—CHR$_6$—C≡C—R$_5$, —CSY, —CSOY;

Y is hydrogen, phenyl, or linear or branched C$_1$–C$_6$alkyl which is unsubstituted or substituted by 1–4 halogen atoms, C$_1$–C$_3$alkoxy or C$_1$–C$_3$alkylthio; C$_2$–C$_6$alkenyl which is unsubstituted or substituted by 1–4 halogen atoms, and R$_3$ is hydrogen, CH$_3$O—, CH$_3$CH$_2$O— or C$_1$–C$_3$alkyl;

R$_4$ is hydrogen or C$_1$–C$_3$alkyl;

R$_5$ is hydrogen, methyl or ethyl;

R$_6$ is hydrogen or methyl.

Halogen is fluoro, chloro, bromo or iodo. Fluoro, chloro and bromo are preferred.

The alkyl groups in the substituent definitions can be straight-chain or branched and are typically methyl, ethyl, n-propyl, isopropyl, n-butyl, sec-butyl, isobutyl, tert-butyl or the different positional isomers of pentyl and hexyl. Said alkyl groups preferably contain 1–3 carbon atoms.

Alkenyl will be understood to mean straight-chain or branched alkenyl, typically vinyl, allyl, methallyl, 1-methylvinyl or but-2-en-1-yl as well as the different positional isomers of pentenyl and hexenyl. Alkenyl radicals having a chain length of up to 3 carbon atoms are preferred.

Haloalkyl is typically fluoromethyl, difluoromethyl, trifluoromethyl, chloromethyl, dichloromethyl, trichloromethyl, 2,2,2-trifluoroethyl, 2-fluoroethyl, 2-chloroethyl and 2,2,2-trichloroethyl, preferably trichloromethyl, difluorochloromethyl, trifluoromethyl and dichlorofluoromethyl.

Alkoxy is typically methoxy, ethoxy, propoxy, isopropoxy. Methoxy and ethoxy are preferred.

Haloalkoxy is typically difluoromethoxy, trifluoromethoxy, 2,2,2-trifluoroethoxy, 1,1,2,2-tetrafluoroethoxy, 2-fluoroethoxy, 2-chloroethoxy and 2,2-difluoroethoxy. Difluoromethoxy, 2-chloroethoxy and trifluoromethoxy are preferred.

Alkylthio is typically methylthio, ethylthio, propylthio, isopropylthio. Methylthio and ethylthio are preferred.

A preferred process is that wherein R$_1$ and R$_2$ are each independently of the other —Y, —COOH, —COY, —CN, —NO$_2$, halogen, —OY, —SO$_2$Y, and Y is hydrogen, phenyl, or linear or branched C$_1$–C$_6$alkyl or C$_2$–C$_6$alkenyl, each of which is unsubstituted or substituted by 1–4 halogen atoms.

Another preferred process is that wherein R$_2$ is hydrogen, and R$_1$ is —Y, —COOH, —COY, —CN, —NO$_2$, halogen, —OY, —SO$_2$Y, wherein Y is hydrogen, phenyl, or linear or branched C$_1$–C$_6$alkyl or C$_2$–C$_6$alkenyl, each of which is unsubstituted or substituted by 1–4 halogen atoms.

In a particularly preferred process, R$_1$ is —Y, —COOH, —COY, —CN, —NO$_2$, halogen, —OY, and Y is hydrogen, phenyl, linear or branched unsubstituted C$_1$–C$_6$alkyl.

To be particularly highlighted is a process wherein R$_1$ is —Y, —COOH, —COY, —OY, and Y is hydrogen, linear or branched unsubstituted C$_1$–C$_6$ alkyl.

The case when R$_1$ is in para-position to the carboxylic acid group gives rise to a particularly preferred subgroup of processes.

Most preferably, R$_1$ is hydrogen, linear or branched C$_1$–C$_3$alkoxy or C$_1$–C$_3$alkyl.

The diazotisation can be carried out in situ by known methods. The introduction of additional anions, such as PF$_6^-$, BF$_4^-$, OAc$^-$, HSO$_4^-$, SO$_4^{2-}$, CH$_3$(C$_6$H$_4$)SO$_3^-$ and CH$_3$SO$_3$, is not necessary. The in situ preparation can also be carried out in the presence of alkyl nitrites, as described in J. Org. Chem. Vol. 46, p. 4885 to 4888 (1981), e.g. with t-butyl nitrite.

The palladium catalysts may be metallic palladium, organic or inorganic palladium compounds. Palladium can be used in the form of palladium black or palladium on a substrate, typically palladium on carbon.

Preferred palladium compounds are palladium salts with chloride, bromide, iodide, nitrate, sulfate, acetate or propionate as anion, or tetrachloropalladium acid or its Li, Na, or K salts, or mixtures thereof.

The novel process can also be carried out using organic palladium complexes. These complexes are preferably prepared in situ.

However, it is also possible to use preformed complexes with palladium. Preferred complexes are: tetrakis(triphenylphosphane)palladium, bis(dibenzylideneacetone)palladium, tris(dibenzylideneacetone)dipalladium, bis(triphenylphosphane)palladium dichloride, bis(benzonitrile)palladium dichloride, or also bis(acetonitrile)palladium dichloride.

The indicated substances can be used as catalysts singly or in any admixture.

Suitable organic solvents are those which are inert during the reaction. The organic solvents are preferably nitriles, alcohols, ethers, ketones, carboxylic acids, acid amides, saturated or unsaturated hydrocarbons, chlorinated hydrocarbons or aromatic compounds, or mixtures thereof.

The organic solvents are preferably miscible with water.

Particularly preferred organic solvents are: $C_1$–$C_6$alcohols, diethyl ether, methyl-tert-butyl ether, tetrahydrofuran, dioxane, dimethoxyethane, ethyl acetate, butyl acetate, acetone, methyl ethyl ketone, methyl isobutyl ketone, cyclohexanone, acetic acid, propionic acid, dimethyl formamide, N-methylpyrrolidone, dimethyl acetamide, sulfolane, dimethyl sulfoxide, acetonitrile, benzonitrile, toluene, xylene, chlorinated $C_1$–$C_6$hydrocarbons, or cyclohexane.

The use of acetonitrile, tetrahydrofuran, ethyl acetate or acetone is very particularly preferred.

Process steps a) and b) can be carried out in water, in organic solvents or in a mixture of both.

It is preferred to carry out reaction steps a) and b) in water or in a mixture of water and acetonitrile, tetrahydrofuran, methanol, ethanol, propanol, ethyl acetate, or acetone, most preferably in a mixture of water and acetonitrile.

The water content, based on the mixture with the organic solvent, can be in the range from 0 to 100% by weight, preferably from 1 to 20% by weight.

The concentration of the ortho-diazonium sulfonate is preferably from 1 to 40% by weight, more particularly from 10 to 20% by weight, based on the entire reaction mixture.

The amount of catalyst is preferably from 0.1 to 5 mol %, more particularly from 0.2 to 2 mol %, based on the ortho-diazonium sulfonate.

The partial pressure of the carbon monoxide is preferably from $10^5$ to $10^7$ pascal, more preferably from $10^5$ to $10^6$ pascal.

The reaction is preferably carried out by introducing carbon monoxide while observing the indicated working pressure. The nitrogen which evolves during the reaction is entrained with the carbon monoxide. The carbon monoxide can be removed by known adsorption processes, e.g. by those disclosed in EP-A-367'618. However, the reaction can also be carried out by forcing in the carbon monoxides at pulsed intervals and by releasing the nitrogen again after each reaction.

Reaction step b) of the process is preferably carried out in the temperature range from –20° C. to 150° C., more particularly from 0° C. to 70° C.

A particularly preferred procedure is that wherein the ortho-diazonium sulfonate of reaction step a) is not isolated, and the second reaction step b) is carried out in the same reaction vessel.

Activated carbon can be added before or after the reaction, and the palladium catalyst can be deposited on the activated carbon in the presence of a reducing agent for the simple separation and recovery of the noble metal. The preferred reducing agent is hydrogen used under normal or overpressure.

If necessary the compounds can be purified in conventional manner, typically by distillation, crystallisation or by chromatographic methods.

The compounds of formula III are important intermediates for the preparation of herbicidally active, as well as plant growth regulating, sulfonylureas, in particular of N-phenylsulfonyl-, N'pyrimidinyl-, N'-triazinyl- and N'-triazolylureas and -thioureas.

Herbicidally active ureas, triazines and pyrimidines are commonly known. Such compounds are disclosed, inter alia, in European patent specifications No. 0 007 687, 0 030 138, 0 073 562 and 0 126 711.

Once the intermediates of formula III are obtained, a great number of possibilities are open to the person skilled in the art to obtain the compounds of formula IV, as is disclosed, inter alia, in EP-A-0 496 701.

Accordingly, the invention also relates to a process for the preparation of compounds of formula IV $$R_1 \underset{R_2}{\underset{|}{\bigcirc}} \begin{matrix} SO_2-NH-\overset{W}{\underset{||}{C}}-\overset{R_{14}}{\underset{|}{N}}-Z \\ C-O-Q \\ || \\ O \end{matrix} \quad (IV)$$

wherein Q is $C_1$–$C_6$alkyl, $C_1$–$C_6$haloalkyl, $C_3$–$C_7$cycloalkyl or heterocycloalkyl, aryl, aralkyl or heteroaryl, $$-\hspace{-4pt}\square\hspace{-4pt} X;$$

or a radical of formula $R_2$ is hydrogen, $R_1$ is —Y, —COOH, COOY, —CONH$_2$, —CONHY, CONY$_2$, C(O)Y, —CN, —NO$_2$, halogen, —OY, —SY, —SOY, —SO$_2$Y, SO$_3$Y, —NHCOY, —NR$_3$R$_4$, —C≡C—R$_5$, —O—CR$_6$H—C≡C—R$_5$, —CSY, —CSOY;

Y is hydrogen, phenyl, or linear or branched $C_1$–$C_6$alkyl which is unsubstituted or substituted by 1–4 halogen atoms, $C_1$–$C_3$alkoxy or $C_1$–$C_3$alkylthio; $C_2$–$C_6$alkenyl which is unsubstituted or substituted by 1–4 halogen atoms;

$R_3$ is hydrogen, CH$_3$O—, CH$_3$CH$_2$O— or $C_1$–$C_3$alkyl;

$R_4$ is hydrogen or $C_1$–$C_3$alkyl;

$R_5$ is hydrogen, methyl or ethyl;

$R_6$ is hydrogen or methyl;

X is oxygen, sulfur, SO or SO$_2$;

W is oxygen or sulfur;

Z is $$Z1: \quad \underset{R_8}{\underset{N}{\overset{R_7}{\underset{\|}{\text{N}}}}}\text{E}$$

$$Z2: \quad \underset{R_{11}}{\underset{N}{\overset{R_{10}}{\underset{\|}{\text{N}}}}}R_9 \quad \text{or}$$

$$Z3: \quad \underset{R_{13}}{\underset{N}{\overset{R_{12}}{\text{N}-\text{N}}}}$$

E is methine or nitrogen;

$R_7$ is $C_1$–$C_4$alkyl, $C_1$–$C_4$alkoxy, $C_1$–$C_4$haloalkoxy, $C_1$–$C_4$haloalkyl, $C_1$–$C_4$haloalkylthio, $C_1$–$C_4$alkylthio, halogen, $C_2$–$C_5$alkoxyalkyl, $C_2$–$C_5$alkoxyalkoxy, amino, $C_1$–$C_3$alkylamino or di($C_1$–$C_3$alkyl)amino;

$R_8$ is $C_1$–$C_4$alkyl, $C_1$–$C_4$alkoxy, $C_1$–$C_4$haloalkoxy, $C_1$–$C_4$haloalkylthio, $C_1$–$C_4$alkylthio, $C_2$–$C_5$alkoxyalkyl, $C_2$–$C_5$alkoxyalkoxy, $C_2$–$C_5$alkylthioalkyl or cyclopropyl;

$R_9$ is hydrogen, fluoro, chloro, methyl, trifluoromethyl, $CH_3O$, $CH_3CH_2O$, $CH_3S$, $CH_3SO$, $CH_3SO_2$ or cyano;

$R_{10}$ is methyl, ethyl, $CH_3O$, $CH_3CH_2O$, fluoro or chloro;

$R_{11}$ is methyl, ethyl, $CH_3O$, $CH_3CH_2O$, fluoro or chloro;

$R_{12}$ is $C_1$–$C_3$alkyl;

$R_{13}$ is $C_1$–$C_3$alkyl, $C_1$–$C_3$alkoxy, chloro or $OCHF_2$;

$R_{14}$ is hydrogen or methyl;

as well as the salts of these compounds; with the provisos that

E is methine, if $R_7$ is halogen; and

E is methine, if $R_7$ or $R_8$ are $OCHF_2$ or $SCHF_2$; by reacting

A) compounds of formula III with $SOCl_2$ and $PCl_5$ to compounds of formula V $$\text{(V)}$$

B) compounds of formula (V) with an alcohol of formula VI Q—OH (VI) to compounds of formula VII $$\text{(VII)}$$

C) compounds of formula VII with ammonia to compounds of formula VIII $$\text{(VIII)}$$

$$\text{(IX)}$$

D) compounds of formula VIII with compounds of formula IX to compounds of formula IV;

which process comprises a) in a first reaction step, diazotising an ortho-aminosulfonic acid of formula I $$\text{(I)}$$

in the presence of an acid and nitrite in water, in an organic solvent or in a mixture thereof, to an ortho-diazonium sulfonate of formula II $$\text{(II)}$$

and, b) in a second reaction step, reacting the ortho-diazonium sulfonate of formula II in the presence of a palladium catalyst in water, an organic solvent or in a mixture thereof, with carbon monoxide, under overpressure, to an ortho-sulfobenzoic acid of formula III $$\text{(III)}$$

wherein $R_2$ is hydrogen, and $R_1$ is independently —Y, —COOH, COOY, —$CONH_2$, —CONHY, $CONY_2$, C(O)Y, —CN, —$NO_2$, halogen, —OY, —SY, —SOY, —$SO_2Y$, $SO_3Y$, —NHCOY, —$NR_3R_4$, —C≡C—$R_5$, —O—$CR_6H$—C≡C—$R_5$, —CSY, —CSOY;

Y is hydrogen, phenyl, or linear or branched $C_1$–$C_6$alkyl which is unsubstituted or substituted by 1–4 halogen atoms, $C_1$–$C_3$alkoxy or $C_1$–$C_3$alkylthio; $C_2$–$C_6$alkenyl which is unsubstituted or substituted by 1–4 halogen atoms, and $R_3$ is hydrogen, $CH_3O$—, $CH_3CH_2O$— or $C_1$–$C_3$alkyl;

$R_4$ is hydrogen or $C_1$–$C_3$alkyl;

$R_5$ is hydrogen, methyl or ethyl;

$R_6$ is hydrogen or methyl.

$C_3$–$C_7$Cycloalkyl is cyclopropyl, cyclobutyl, cyclopentyl, cyclohexyl or cycloheptyl.

The invention also embraces those salts which are able to form the compounds of formula IV with amines, alkali metal bases and alkaline earth metal bases or quaternary ammonium bases.

The alkali metal hydroxides and alkaline earth metal hydroxides meriting particular interest include the hydroxides of lithium, sodium, potassium, magnesium or calcium. The hydroxides of sodium or potassium are of very special interest.

Illustrative examples of amines suitable for salt formation are primary, secondary and tertiary aliphatic and aromatic amines, typically methylamine, ethylamine, propylamine, isopropylamine, the four isomeric butylamines, dimethylamine, diethylamine, diethanolamine, dipropylamine, diisopropylamine, di-n-butylamine, pyrrolidine, piperidine, morpholine, trimethylamine, triethylamine, tripropylamine, quinuclidine, pyridine, quinoline and isoquinoline. Ethylamine, propylamine, diethylamine or triethylamine are preferred, and isopropylamine and diethanolamine are most preferred.

Illustrative examples of quaternary ammonium bases are usually the cations of haloammonium salts, typically the tetramethylammonium cation, the trimethylbenzylammonium cation, the triethylbenzylammonium cation, the tetraethylammonium cation, the trimethylethylammonium cation, and also the ammonium cation.

Among the compounds of formula IV, those compounds are preferred wherein W is oxygen; Z is preferably Z1; X is preferably oxygen or sulfur, more particularly oxygen, and E is nitrogen.

Also to be highlighted is that group of compounds of formula IV wherein Z is Z1; X is oxygen or sulfur, more particularly oxygen, and E is methine.

Among these two groups of compounds of formula IV, those compounds are of particular interest wherein $R_1$ is hydrogen, fluoro, chloro, $OCH_3$, $OCHF_2$, methyl, $SCH_3$, methoxy, ethoxy or chloroethoxy;

$R_8$ is $C_1$–$C_3$alkyl, $C_1$–$C_3$alkoxy, $C_1$–$C_2$haloalkoxy, trifluoromethyl, $CHF_2$, $CH_2F$, $CH_2OCH_3$, fluoro, chloro, $NH_2$, $NHCH_3$, $N(CH_3)_2$, $SCH_3$ or $CH_2OCH_3$; and $R_9$ is $C_1$–$C_3$alkyl, $C_1$–$C_3$alkoxy, $C_1$–$C_2$haloalkoxy or cyclopropyl.

In particularly preferred compounds of this group $R_1$ is hydrogen;

$R_8$ is methyl, ethyl, $OCH_3$, $OC_2H_5$, $OCHF_2$, $OCH_2CF_3$, chloro, $NHCH_3$, $N(CH_3)_2$ or $CH_2OCH_3$; and $R_9$ is methyl, $OCH_3$, $OCHF_2$, $OC_2H_5$ or cyclopropyl.

In a further preferred subgroup of compounds of formula IV

W is oxygen;

Z is Z1;

X is sulfur;

$R_1$ is hydrogen, fluoro, chloro, $OCH_3$, $OCHF_2$, methyl or methylthio;

$R_8$ is $C_1$–$C_3$alkyl, $C_1$–$C_3$alkoxy, $C_1$–$C_2$haloalkoxy, $CF_3$, $CHF_2$, $CH_2F$, $CH_2OCH_3$, fluoro, chloro, $NH_2$, $NHCH_3$, $N(CH_3)_2$, $SCH_3$ or $CH_2OCH_3$; and $R_9$ is $C_1$–$C_3$alkyl, $C_1$–$C_3$alkoxy, $C_1$–$C_2$haloalkoxy or cyclopropyl.

Among this group, those compounds of formula IV are of interest wherein

W is oxygen;

Z is Z1;

X is sulfur;

$R_1$ is hydrogen;

$R_8$ is methyl, ethyl, $OCH_3$, $OC_2H_5$, $OCHF_2$, $OCH_2CF_3$, Cl, $NHCH_3$, $N(CH_3)_2$ or $CH_2OCH_3$; and $R_9$ is methyl, $OCH_3$, $OCHF_2$, $OC_2H_5$ or cyclopropyl.

The preferred single compounds within the scope of formula IV prepared according to the novel process are:

N-[2-(oxetane-3-oxycarbonyl)]phenylsulfonyl-N'-(4-methoxy-6-methyl-1,3,5-triazinyl)urea, N-[2-(oxetane-3-oxycarbonyl)-5-methoxy] phenylsulfonyl-N'-(4-methoxy-6-methyl-1,3,5-triazinyl)urea, N-[2-(oxetane-3-oxycarbonyl)]phenylsulfonyl-N'-(4,6-dimethyl-pyrimidin-2-yl)urea, N-[2-(oxetane-3-oxycarbonyl)]phenylsulfonyl-N'-(4-methoxy-6-methyl-pyrimidin-2-yl)urea, or N-[2-(oxetane-3-oxycarbonyl)]phenylsulfonyl-N'-(4,6-dimethoxy-pyrimidin-2-yl)urea.

The following Examples illustrate the invention.

EXAMPLE 1

Preparation of 4-methoxybenzoic acid-2-sulfonic acid a) Diazotisation of 4-methoxyaniline-2-sulfonic acid With cooling, 48 g of 4-methoxyaniline-2-sulfonic acid are added to 100 ml of deionised water and 100 ml of 37% hydrochloric acid. The mixture is cooled to 10° C. and a solution of 10.4 g of sodium nitrite in 20 ml of water is added at this temperature. When the addition is complete, the mixture is stirred for 1 hour and 5.6 g of sulfamic acid are then added. The precipitated diazonium salt is isolated by filtration and washed with 20 ml each of 2N hydrochloric acid, methanol and diethyl ether. The pale brown crystals are dried at room temperature.

b) Preparation of 4-methoxybenzoic acid-2-sulfonic acid

An agitated autoclave is charged with 8 g of the diazonium compound prepared under a) in 33 g of acetonitrile and 6.7 g of deionised water. To this mixture are added 66.2 mg of palladium(II) chloride (corresponding to 1 mol %) and the reaction vessel is rendered inert with nitrogen. Subsequently, carbon monoxide is forced in under a pressure of 8 bar and the suspension is heated to 65° C. and stirred at this temperature for 6 hours. The reaction mixture is then cooled, rendered inert with nitrogen, and 0.5 g of activated carbon is then added. Hydrogen is forced in under a pressure of 0.1 bar and the suspension is stirred for 2 hours at room temperature. The carbon is removed by filtration and washed with water, 97% of the palladium remaining thereon. The filtrate is concentrated by evaporation, to give 10.1 g of crude product containing 84.6% of 4-methoxybenzoic acid-2-sulfonic acid, according to HPLC analysis, corresponding to 97.5% of theory.

Melting point: 122° C. (clear point), sinters at 98°–100° C.

$^1$H-NMR: (DMSO, 250 Mhz) 3.94 ppm (s, 3H); 7.16 ppm (m, 1H); 7.47 ppm (m, 1H); 7.93 ppm (m, 1H)

EXAMPLE 2

One-pot process for the preparation of 4-methoxybenzoic acid-2-sulfonic acid

A glass reactor is charged with 5 g of 4-methoxyaniline-2-sulfonic acid to which 3.7 g of sulfuric acid in 30 ml of water are added. To this mixture are added 25 ml of acetonitrile and the mixture is then cooled to 0°–5° C. A solution of 2 g of sodium nitrite in 5 ml of water is added dropwise at this temperature. The suspension is stirred for 1 h and 2 g of sulfamic acid are then added. Subsequently, 43.6 mg of palladium(II) chloride with 5 ml of acetonitrile are flushed into the reactor, which is then rendered inert with argon. The carbon monoxide is then forced in under a pressure of 8 bar and the reaction mixture is heated to 65° C. After 6 h, the reaction mixture is cooled and filtered. The content of 4-methoxybenzoic acid -2-sulfonic acid in the filtrate is 7.58% according to HPLC analysis, corresponding to a yield of 88% of theory.

EXAMPLE 3

Preparation of 2-sulfobenzoic acid a) Diazotisation of orthanilic acid 5.1 g of orthanilic acid 100% are suspended in 20 ml of acetic acid. A solution of 2.4 g of sodium nitrite in 5 ml of water is added dropwise at 15° C. When the addition is complete, the mixture is stirred for 1 h and a solution of 0.7 g of sulfamic acid in 5 ml of water is then added. Excess solvent is decanted off and replaced with acetonitrile. This procedure is repeated several times.

b) Preparation of 2-sulfobenzoic acid

To the decanted diazo residue are added 30 ml of acetonitrile and 181 mg of palladium(II) acetate. The reactor is rendered inert with nitrogen. Carbon monoxide is then forced in under a pressure of 8 bar and the reaction mixture is stirred overnight at room temperature. 30 ml of water are added to the reaction mixture, which is then filtered, to give 85.4 g of product solution containing 4.35% of 2-sulfobenzoic acid according to HPLC analysis, corresponding to a yield of 62.4% of theory. For characterisation, the filtrate is concentrated on a rotary evaporator. The brown residue is dissolved in acetonitrile and stirred. The resulting suspension is filtered and the residue is characterised.

$^1$H-NMR: (DMSO, 250 MHz) 7.95 ppm (1H, m); 7.84 ppm (1H,m); 7.63 ppm (2H,m)

What is claimed is:

1. A process for the preparation of aromatic ortho-sulfocarboxylic acids, which comprises
   a) in a first reaction step, diazotising an aromatic ortho-aminosulfonic acid in the presence of an acid and nitrite in water, in an organic solvent or in a mixture thereof, to an ortho-diazonium sulfonate,
   b) in a second reaction step, reacting the ortho-diazonium sulfonate in the presence of a palladium catalyst in water alone or in a mixture with an organic solvent, with carbon monoxide, under overpressure, to an aromatic ortho-sulfocarboxylic acid; wherein the palladium catalyst is selected from the group consisting of a palladium salt with chloride, bromide, iodide, nitrate, or sulfate anions, a tetrachloropalladium acid or the Li, Na, or K salt thereof, and a mixture thereof.

2. A process according to claim 1, which further comprises
   c) in a third step, adding activated carbon before or after the reaction;
   d) in a fourth step, depositing the palladium catalyst on the activated carbon in the presence of a reducing agent; and
   e) in a fifth step, separating and recovering the deposited palladium.

3. A process according to claim 2, wherein the reducing agent is hydrogen used under normal or overpressure.

4. A process according to claim 1, wherein two substituents $R_1$ and $R_2$ are attached at the aromatic radical of the ortho-aminosulfonic acid, and $R_1$ and $R_2$ are each independently of the other —Y, —COOH, COOY, —CONH$_2$, —CONHY, —CONY$_2$, —C(O)Y, —CN, —NO$_2$, halogen, —OY, —SY, —SOY, —SO$_2$Y, SO$_3$Y, —NHCOY, —NR$_3$R$_4$, —C≡C—R$_5$, —O—CHR$_6$—C≡C—R$_5$, —CSY, —CSOY;

Y is hydrogen, phenyl, or linear or branched $C_1$–$C_6$alkyl which is unsubstituted or substituted by 1–4 halogen atoms, $C_1$–$C_3$alkoxy or $C_1$–$C_6$alkylthio; $C_2$–$C_6$alkenyl which is unsubstituted or substituted by 1–4 halogen atoms, and $R_3$ is hydrogen, CH$_3$O—, CH$_3$CH$_2$O— or $C_1$–$C_3$alkyl;

$R_4$ is hydrogen or $C_1$–$C_3$alkyl;

$R_5$ is hydrogen, methyl or ethyl;

$R_6$ is hydrogen or methyl.

5. A process according to claim 1, which comprises
   a) in a first reaction step, diazotising an aromatic ortho-aminosulfonic acid of formula I

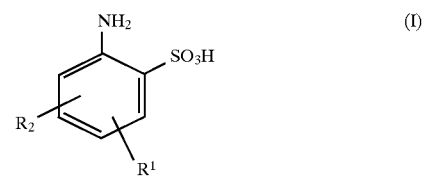

in the presence of an acid and nitrite in water, in an organic solvent or in a mixture thereof, to an ortho-diazonium sulfonate of formula II

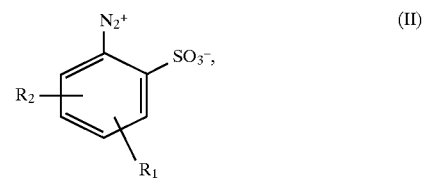

and,
   b) in a second reaction step, reacting the ortho-diazonium sulfonate of formula II in the presence of a palladium catalyst in water, in an organic solvent or in a mixture thereof, with carbon monoxide, under overpressure, to an ortho-sulfobenzoic acid of formula III

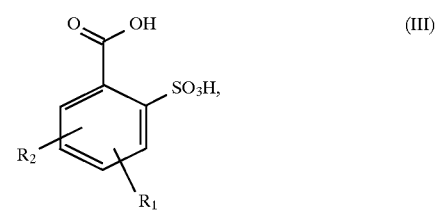

wherein $R_1$ and $R_2$ are each independently of the other —Y, —COOH, COOY, —CONH$_2$, —CONHY, —CONY$_2$, —C(O)Y, —CN, —NO$_2$, halogen, —OY, —SY, —SOY, —SO$_2$Y, SO$_3$Y, —NHCOY, —NR$_3$R$_4$, —C≡C—R$_5$, —O—CHR$_6$—C≡C—R$_5$, —CSY, —CSOY;

Y is hydrogen, phenyl, or linear or branched $C_1$–$C_6$alkyl which is unsubstituted or substituted by 1–4 halogen atoms, $C_1$–$C_3$alkoxy or $C_1$–$C_3$alkylthio; $C_2$–$C_6$alkenyl which is unsubstituted or substituted by 1–4 halogen atoms, and $R_3$ is hydrogen, $CH_3O$—, $CH_3CH_2O$— or $C_1$–$C_3$alkyl;

$R_4$ is hydrogen or $C_1$–$C_3$alkyl;

$R_5$ is hydrogen, methyl or ethyl;

$R_6$ is hydrogen or methyl.

6. A process according to claim 5, wherein $R_1$ and $R_2$ are each independently of the other —Y, —COOH, —COY, —CN, —NO$_2$, halogen, —OY, —SO$_2$Y, and Y is hydrogen, phenyl, or linear or branched $C_1$–$C_6$alkyl or $C_2$–$C_6$alkenyl, each of which is unsubstituted or substituted by halogen.

7. A process according to claim 6, wherein $R_2$ is hydrogen, and $R_1$ is —Y, —COOH, —COY, —CN, —NO$_2$, halogen, —OY, —SO$_2$Y, and Y is hydrogen, phenyl, linear or branched $C_1$–$C_6$alkyl or $C_2$–$C_6$alkenyl, each of which is unsubstituted or substituted by 1–4 halogen atoms.

8. A process according to claim 7, wherein $R_1$ is —Y, —COOH, —COY, —CN, —NO$_2$, halogen, —OY, and Y is hydrogen, phenyl, unsubstituted linear or branched $C_1$–$C_6$alkyl.

9. A process according to claim 8, wherein $R_1$ is —Y, —COOH, —COY, —OY, and Y is hydrogen, unsubstituted linear or branched $C_1$–$C_6$alkyl.

10. A process according to claim 9, wherein $R_1$ is in para-position to the carboxylic acid group.

11. A process according to claim 10, wherein $R_1$ is hydrogen, linear or branched $C_1$–$C_3$alkoxy or $C_1$–$C_3$alkyl.

12. A process according to claim 1, wherein the organic solvent is selected from the group consisting of nitriles, alcohols, ethers, ketones, carboxylic acids, acid amides, saturated and unsaturated hydrocarbons, chlorinated hydrocarbons and aromatic compounds, and mixtures thereof.

13. A process according to claim 12, wherein the solvent is selected from the group consisting of $C_1$–$C_6$alcohols, diethyl ether, methyl-tert-butyl ether, tetrahydrofuran, dioxane, dimethoxyethane, ethyl acetate, butylacetate, acetone, methyethylketone, methylisobutylketone, cyclohexanone, acetic acid, propionic acid, dimethylformamide, N-methylpyrrolidone, dimethylacetamide, sulfolane, dimethylsulfoxide, acetonitrile, benzonitrile, toluene, xylene, chlorinated $C_1$–$C_6$hydrocarbons, and cyclohexane.

14. A process according to claim 13, wherein the solvent is selected from the group consisting of acetonitrile, tetrahydrofuran, ethyl acetate and acetone.

15. A process according to claim 1, which comprises using in reaction step b) a mixture of water and acetonitrile, tetrahydrofuran, methanol, ethanol, propanol, ethyl acetate, or acetone.

16. A process according to claim 1, wherein the mono- or polysubstituted ortho-diazonium sulfonate of reaction step a) is not isolated, and the second reaction step b) is carried out in the same reaction vessel.

17. A process according to claim 1, wherein activated carbon is added when the reaction is complete and the palladium catalyst is deposited reductively on the activated carbon in the presence of hydrogen under overpressure.

18. A process for the preparation of a compound of formula IV

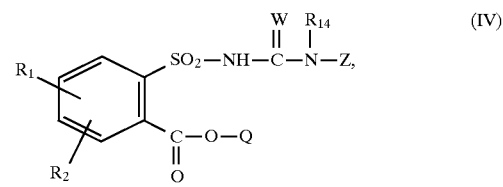

wherein

Q is $C_1$–$C_6$alkyl, $C_1$–$C_6$haloalkyl, $C_3$–$C_7$cycloalkyl or heterocycloalkyl, aryl, aralkyl or heteroaryl,

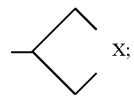

or a radical of formula $R_2$ is hydrogen, $R_1$ is —Y, —COOH, COOY, —CONH$_2$, —CONHY, CONY$_2$, C(O)Y, —CN, —NO$_2$, halogen, —OY, —SY, —SOY, —SO$_2$Y, SO$_3$Y, —NHCOY, —NR$_3$R$_4$, —C≡C—R$_5$, —O—CR$_6$H—C≡C—R$_5$, —CSY, —CSOY;

Y is hydrogen, phenyl, or linear or branched $C_1$–$C_6$alkyl which is unsubstituted or substituted by 1–4 halogen atoms, $C_1$–$C_3$alkoxy or $C_1$–$C_3$alkylthio; $C_2$–$C_6$alkenyl which is unsubstituted or substituted by 1–4 halogen atoms;

$R_3$ is hydrogen, $CH_3O$—, $CH_3CH_2O$— or $C_1$–$C_3$alkyl;

$R_4$ is hydrogen or $C_1$–$C_3$alkyl;

$R_5$ is hydrogen, methyl or ethyl;

$R_6$ is hydrogen or methyl;

X is oxygen, sulfur, SO or SO$_2$;

W is oxygen or sulfur;

Z is

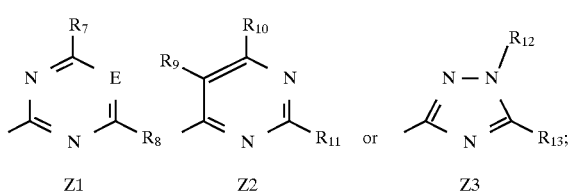

E is methine or nitrogen;

$R_7$ is $C_1$–$C_4$alkyl, $C_1$–$C_4$alkoxy, $C_1$–$C_4$haloalkoxy, $C_1$–$C_4$haloalkyl, $C_1$–$C_4$haloalkylthio, $C_1$–$C_4$alkylthio, halogen, $C_2$–$C_5$alkoxyalkyl, $C_2$–$C_5$alkoxyalkoxy, amino, $C_1$–$C_3$alkylamino or di($C_1$–$C_3$alkyl)amino;

$R_8$ is $C_1$–$C_4$alkyl, $C_1$–$C_4$alkoxy, $C_1$–$C_4$haloalkoxy, $C_1$–$C_4$haloalkylthio, $C_1$–$C_4$alkylthio, $C_2$–$C_5$alkoxyalkyl, $C_2$–$C_5$alkoxyalkoxy, $C_2$–$C_5$alkylthioalkyl or cyclopropyl;

$R_9$ is hydrogen, fluoro, chloro, methyl, trifluoromethyl, $CH_3O$, $CH_3CH_2O$, $CH_3S$, $CH_3SO$, $CH_3SO_2$ or cyano;

$R_{10}$ is methyl, ethyl, $CH_3O$, $CH_3CH_2O$, fluoro or chloro;

$R_{11}$ is methyl, ethyl, $CH_3O$, $CH_3CH_2O$, fluoro or chloro;

$R_{12}$ is $C_1$–$C_3$alkyl;

$R_{13}$ is $C_1$–$C_3$alkyl, $C_1$–$C_3$alkoxy, chloro or $OCHF_2$;

$R_{14}$ is hydrogen or methyl;

as well as the salt thereof;

with the provisos that

E is methine, if $R_7$ is halogen; and

E is methine, if $R_7$ or $R_8$ are $OCHF_2$ or $SCHF_2$;

by reacting

A) a compound of formula III with $SOCl_2$ and $PCl_5$ to a compound of formula V

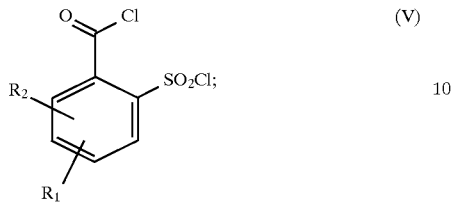

B) a compound of formula (V) with an alcohol of formula VI Q—OH (VI) to a compound of formula VII

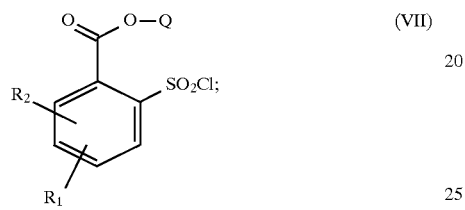

C) a compound of formula VII with ammonia to a compound of formula VIII

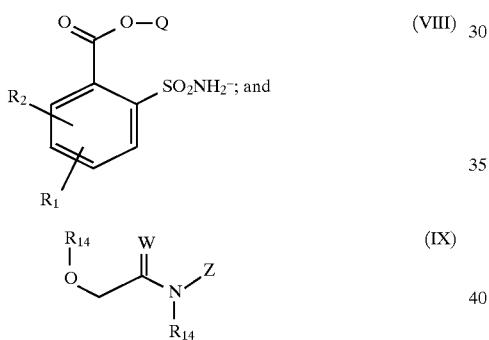

D) a compound of formula VII with a compound of formula IX to a compound of formula IV;

which process comprises a) in a first reaction step, diazotising an ortho-aminosulfonic acid of formula I

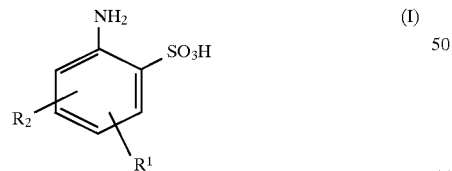

in the presence of an acid and nitrite in water, in an organic solvent or in a mixture thereof, to an ortho-diazonium sulfonate of formula II

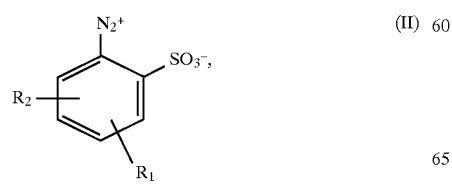

and, b) in a second reaction step, reacting the ortho-diazonium sulfonate of formula II in the presence of a palladium catalyst in water alone or in a mixture with an organic solvent, with carbon monoxide, under overpressure, to an ortho-sulfobenzoic acid of formula III

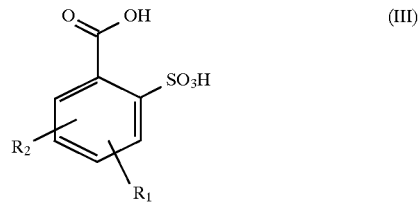

wherein $R_2$ is hydrogen, and $R_1$ is independently —Y, —COOH, COOY, —CONH$_2$, —CONHY, CONY$_2$, C(O)Y, —CN, —NO$_2$, halogen, —OY, —SY, —SOY, —SO$_2$Y, SO$_3$Y, —NHCOY, —NR$_3$R$_4$, —C≡C—R$_5$, —O—CR$_6$H—C≡C—R$_5$, —CSY, —CSOY;

Y is hydrogen, phenyl, or linear or branched $C_1$–$C_6$alkyl which is unsubstituted or substituted by 1–4 halogen atoms, $C_1$–$C_3$alkoxy or $C_1$–$C_3$alkylthio; $C_2$–$C_6$alkenyl which is unsubstituted or substituted by 1–4 halogen atoms, and $R_3$ is hydrogen, $CH_2O$—, $CH_3CH_2O$— or $C_1$–$C_3$alkyl;

$R_4$ is hydrogen or $C_1$–$C_3$alkyl;

$R_5$ is hydrogen, methyl or ethyl;

$R_6$ is hydrogen or methyl; and wherein the palladium catalyst is selected from the group consisting of a palladium salt with chloride, bromide, iodide, nitrate, or sulfate anions, a tetrachloropalladium acid or the Li, Na, or K salt thereof, and a mixture thereof.

19. A process according to claim 18, which further comprises c) in a third step, adding activated carbon before or after the reaction;

d) in a fourth step, depositing the palladium catalyst on the activated carbon in the presence of a reducing agent; and e) in a fifth step, separating and recovering the deposited palladium.

20. A process according to claim 19, wherein the reducing agent is hydrogen used under normal or overpressure.

21. A process according to claim 18 for the preparation of

N-[2-(oxetane-3-oxycarbonyl)]phenylsulfonyl-N'-(4-methoxy-6-methyl-1,3,5-triazinyl)urea, N-[2-(oxetane-3-oxycarbonyl)-5-methoxy]phenylsulfonyl-N'-(4-methoxy-6-methyl-1,3,5-triazinyl)urea, N-[2-(oxetane-3-oxycarbonyl)]phenylsulfonyl-N'-(4,6-dimethyl-pyrimidin-2-yl)urea, N-[2-(oxetane-3-oxycarbonyl)]phenylsulfonyl-N'-(4-methoxy-6-methyl-pyrimidin-2-yl)urea, or N-[2-(oxetane-3-oxycarbonyl)]phenylsulfonyl-N'-(4,6-dimethoxy-pyrimidin-2-yl)urea.

* * * * *